United States Patent
Rousseau et al.

(10) Patent No.: US 7,678,332 B2
(45) Date of Patent: Mar. 16, 2010

(54) DRIVE ARRANGEMENTS FOR A STRIP OF CUVETTES IN ANALYTICAL DEVICE

(75) Inventors: Alain Rousseau, Paris (FR); Khaled Abou-Saleh, Courbevoie (FR)

(73) Assignee: Diagnostica Stago, Gennevilliers (FR)

( * ) Notice: Subject to any disclaimer, the term of this patent is extended or adjusted under 35 U.S.C. 154(b) by 0 days.

(21) Appl. No.: 12/033,796

(22) Filed: Feb. 19, 2008

(65) Prior Publication Data
US 2009/0120769 A1    May 14, 2009

Related U.S. Application Data

(63) Continuation of application No. 10/503,238, filed as application No. PCT/FR03/00256 on Jan. 28, 2003, now abandoned.

(30) Foreign Application Priority Data

Feb. 1, 2002   (FR) ................................. 02 01236

(51) Int. Cl.
*G01N 35/02* (2006.01)
*G01N 35/04* (2006.01)
(52) U.S. Cl. .............................. 422/65; 422/63; 422/64; 422/68.1; 422/82.05; 436/43; 436/48; 436/49; 436/165; 198/418; 198/846

(58) Field of Classification Search ....................... None
See application file for complete search history.

(56) References Cited

U.S. PATENT DOCUMENTS

| 4,168,775 A | | 9/1979 | Mueller |
| 4,200,000 A | | 4/1980 | Fliiehmann |
| 4,731,225 A | | 3/1988 | Wakatake |
| 4,867,308 A | * | 9/1989 | Crawford et al. ............ 206/714 |
| 5,849,247 A | * | 12/1998 | Uzan et al. ..................... 422/65 |
| 6,328,164 B1 | | 12/2001 | Rickkinen et al. |
| 6,767,511 B1 | | 7/2004 | Rousseau |

FOREIGN PATENT DOCUMENTS

| EP | 0 837 331 A1 | 4/1998 |
| JP | 01-158356 A | 6/1989 |
| WO | WO 99/64839 A1 | 12/1999 |

\* cited by examiner

*Primary Examiner*—P. Kathryn Wright
(74) *Attorney, Agent, or Firm*—Browdy & Neimark, PLLC

(57) ABSTRACT

The invention relates to a drive arrangement for a series of cuvettes (C) forming a strip (2) fixed by means of a film (3) in an automatic analytical device (1), comprising at least one toothed belt (12), the teeth of which engage with the corresponding forms of the cuvettes. The above finds application in an automatic analytical device, particularly for the determination of the rate of change of the physical state of a medium.

7 Claims, 2 Drawing Sheets

DRIVE ARRANGEMENTS FOR A STRIP OF CUVETTES IN ANALYTICAL DEVICE

The present invention concerns an improvement of an automatic analysis device able to be used, especially for determining the modification times of a medium in a physical state.

This device is particularly, but not exclusively, applicable to determination of the blood coagulation time in accordance with a process according to which the blood sample is placed at the bottom of a bowl containing a ferromagnetic ball driven in a periodic movement under the effect of an external magnetic field. The modifications of the movements of the ferromagnetic ball (for example the amplitude and/or frequency variations), which are representative of changes of the physical state of the blood, are then detected with the aid of suitable means.

This type of device is described in the patent EP 0 325 874 filed in the name of the Diagnostica Stago company.

It comprises a bowl distributor for sole usage, each bowl comprising a bent inward bottom constituting the rolling path of the ball, and a face opposite the bottom having an opening. Transversal edges of this opening extend two shoulders at a right angle with respect to the faces of the bowls. The bowls are placed side by side and fixed on a flexible support strip which seals off their openings but said bowls can be removed. The strip equipped with bowls can be wound onto a coil able to be engaged on an element provided in a storage and distribution compartment of the device. The bowls run off one by one into a detection station.

It proves that this solution has the drawback of not guaranteeing a proper positioning of the bowl in the detection station. The analysis of the movements of the ball thus risks being false. This therefore may lead to there being a risk of error concerning the result of the analysis.

The object of the invention is thus to eliminate these drawbacks.

To this effect, the invention concerns a device for moving a set of bowls forming a strip and joined together by a film in an automatic analysis device comprising at least one notched belt whose serrations gear with suitable adaptations of the bowls.

Advantageously, said bowls may have an opening at the level of which two opposing shoulders extend and projecting outside of the bowl on which said adaptations are embodied.

In addition, said shoulders may each have two oblique edges with respect to the longitudinal axis of the strip so that the unit formed by the strip and bowls has two serrated lateral edges.

Thus, the bowls/strip unit has a rack function.

Moreover, the lateral borders of the film each have a serrated profile whose teeth are accentuated by the presence of the bowl shoulders.

By means of the gearing of the serrations of the belt between the teeth of the unit formed by the film and the bowls, the movement makes it possible to index the position of the bowls.

This device exhibits no play during handling in either direction.

One embodiment of the invention is shown hereafter and given by way of non-restrictive example with reference to the accompanying drawings on which:

In this example, the automatic analysis device introduces a bowl feeding comprising a series of about a hundred bowls C forming a strip 2.

Figure 1:
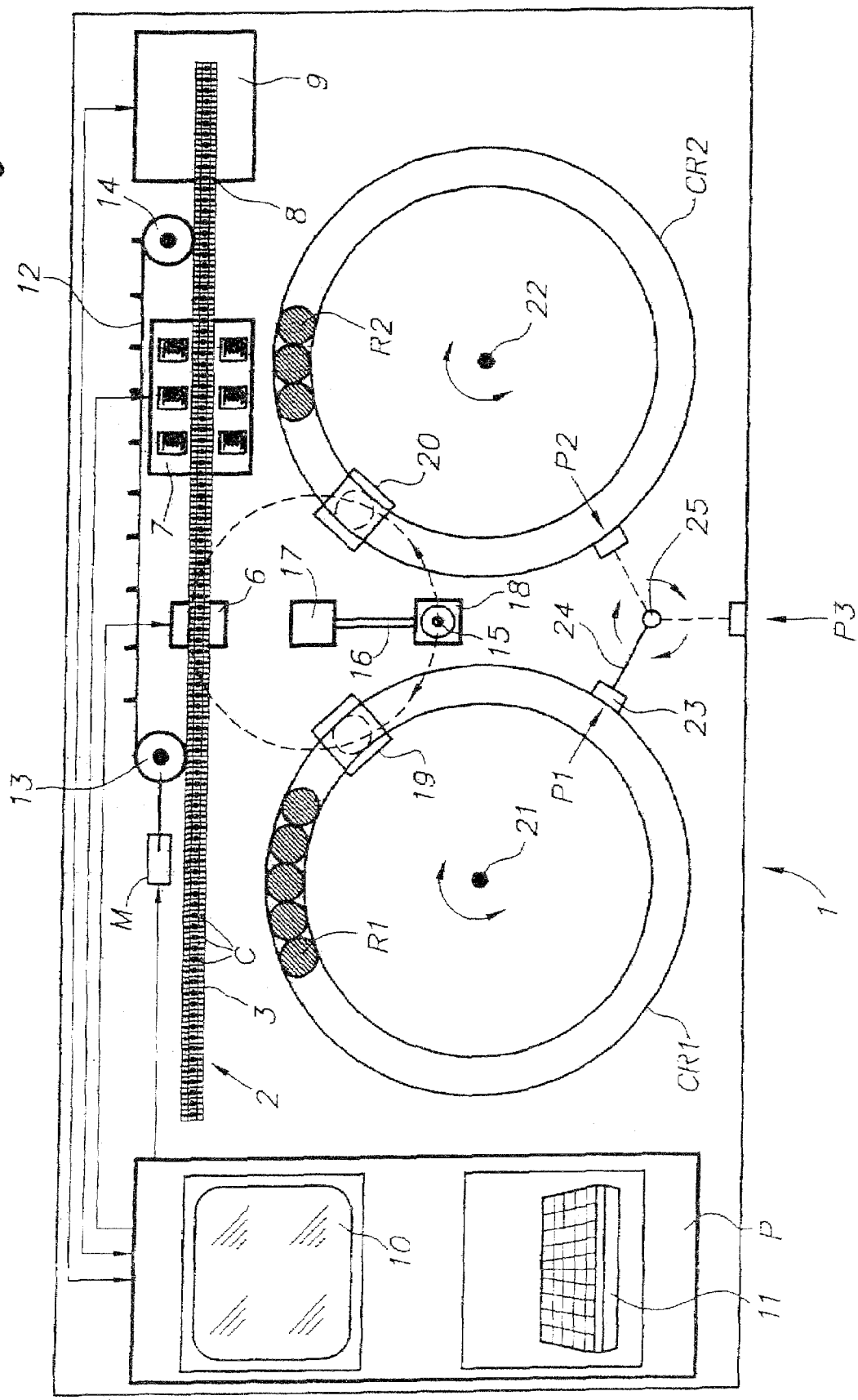
FIG. 1 is a diagrammatic representation of an automatic analysis device of medium size.
Figure 2:
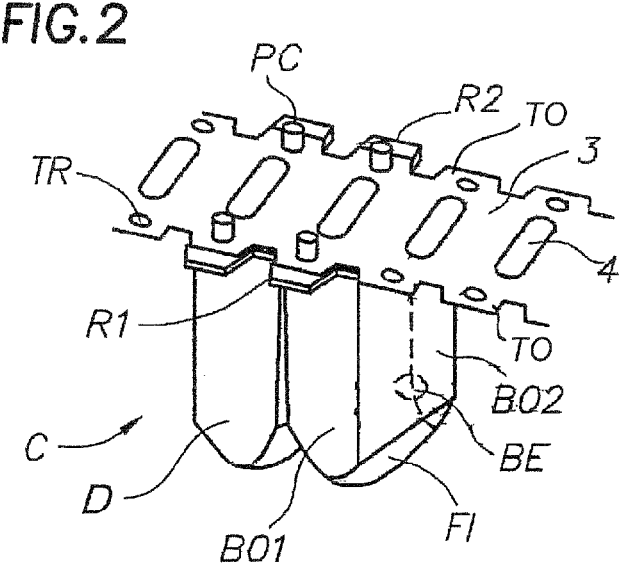
FIG. 2 is a diagrammatic perspective view of a bowl mounted on the film.
Figure 3:
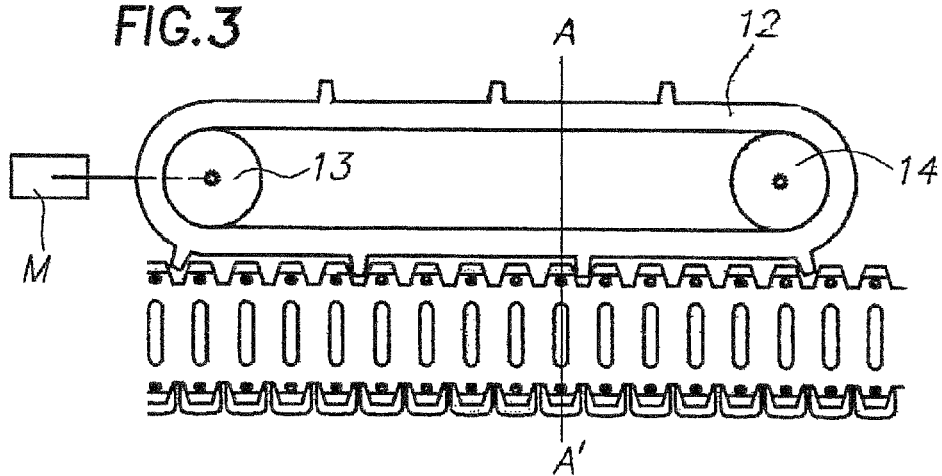
FIG. 3 is a diagrammatic top view of the film equipped with its bowls and the rack drive system.

As shown on FIG. 2, the bowls C embodied by moulding a transparent plastic material each have a parallelpiped flat-shaped body whose bent inward bottom FI constitutes a rolling path for a ferromagnetic ball BE. Opposite this bottom FI, the bowl C has an opening at the level of which its two opposing edges $BO_1$, $BO_2$ are extended at a right angle by two respective shoulders $R_1$, $R_2$ each provided with a cylindrical protuberance PC extending from the side opposite the body. These two protuberances are intended to be engaged forcefully in two respective holes TR respectively provided on the two lateral borders of the film. The shoulders $R_1$, $R_2$ have for example the shape of a rectangular trapezium whose large base is integral with the bowl. The lateral borders of a support film 3 then have in the gaps of the shoulders $R_1$, $R_2$ of successive bowls trapezoid cuts whose oblique edges extend to the right of the oblique edges of the shoulders $R_1$, $R_2$. By means of these arrangements, the lateral borders of the film each have a serrated profile whose teeth are accentuated by the presence of the shoulders $R_1$, $R_2$ of the bowls.

The film is flexible and is constituted by an absorbent material, such as paper. The top of each bowl is pierced with an orifice 4 so as to allow the passage of a pipette.

Figure 4:
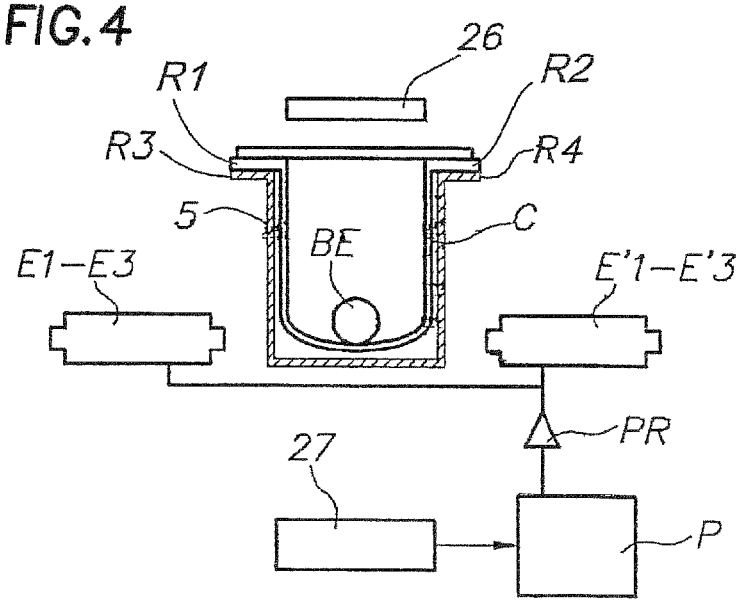
FIG. 4 is a vertical diagrammatic section along A/A of FIG. 3.

According to the device shown on FIG. 4, the strip of bowls 2 is guided by a rail 5. This rail has a U-shaped cross section whose two vertical wings are extended at a right angle by two shoulders $R_3$, $R_4$, the shoulders $R_1$, $R_2$ of the bowls resting on the shoulders $R_3$, $R_4$. The strip successively passes through a pipette station 6, a detection station 7 and a cutting station 8 at the outlet of which each bowl is recovered in a container 9 provided for this purpose.

The functioning of these various stations is controlled by a processor P comprising a central unit and peripheral units, such as a screen 10/keyboard 11 unit.

The movement of the film is provided by a drive mechanism introducing an endless belt 12 guided at each extremity by rollers 13, 14, one of the latter being driven in rotation by a step motor M. This belt comprises a serration whose notches are spaced by a distance equal to a multiple of the width of the bowls (for example 4-5 bowls). These notches have an involute to a circle profile which corresponds to a normal teeth-shaped rack so as to fully gear between the teeth of the serrated profile of the strip; these teeth thus accurately move the strip of bowls with automatic centering and compensation of any possible play (the notches being more or less engaged deeply between said teeth).

The pipette station 6 is controlled by an automated height-adjustable vertical pipette 15 so as to be able to assume a lower rinsing or pipette position and an upper position allowing it to move inside a horizontal plane.

This pipette 15 is fixed at one of its extremities of an arm 16 mounted rotating by its other extremity around a vertical spindle 17. The driving in rotation of the arm 16 is ensured by a motor controlled by the processor P.

By means of this particularly simple mechanism, the pipette 15 can be successively brought to the pipette area of the pipette station 6, a rinsing area 18 diametrically opposite, and to two sampling areas 19, placed symmetrically with respect to the axis passing through the pipette area 6 and the rinsing area 18.

The sampling areas 19, 20 are situated inside the path of the receptacles $R_1$, $R_2$ borne by two respective carrousels $CR_1$, $CR_2$ moving in rotation around two vertical spindles 21, 22 and controlled by two motors controlled by the processor P.

One of these carrousels $CR_1$ is used to contain the receptacles of the blood samples to be analysed, whereas the other carrousel $CR_2$ contains the receptacles $R_2$ allocated to the various reactive agents able to be used within the context of the analyses it is desired to carry out.

Of course, the processor P is programmed so as to control pipette sequences appropriate to the nature of the analyses to be conducted and possible successively comprising:

a prior rinsing of the pipette 15, the taking of a sample dose contained in one of the receptacles $R_1$ of the carrousel $CR_1$, the injection of this dose into a bowl C situated in the pipette station 6, the rinsing of the pipette 15, the taking of a reactive agent dose contained in one of the receptacles $R_2$ of the carrousel $CR_2$, the injection of this reactive agent dose into the bowl C, the identification of the blood samples to be analysed and that of the reactive agents being automatically carried out by means of a bar code reader 23 able to carry out reading of the bar codes present on the receptacles $R_1$, $R_2$ borne by the carrousels $CR_1$, $CR_2$.

In this example, for these readings, the sole bar code reader 23 is mounted at the extremity of an arm 24 pivoting around a vertical spindle 25 so as to be able to occupy three positions, namely:

a position $P_1$ for reading the bar codes of the receptacles $R_1$ of the carrousel $CR_1$, a position $P_2$ for reading the bar codes of the receptacles $R_2$ of the carrousel $CR_2$, and a position $P_3$ for reading the receptacles placed by the operator in a reading station, for example so as to enter information exploited by the processor within the context of functioning of the device.

The measuring station 7 here comprises three successive measuring positions each comprising (FIG. 4) a pair of coaxial electromagnets $E_1$, $E'_1$-$E_2$, $E'_2$-$E_3$, $E'_3$ situated on both sides of the film 3 at the right of the lateral faces of the bowls C.

The station 7 also comprises:

an infrared light source 26 situated above the bowl, an electronic camera 27 situated below the bowls borne by the film on which the image of the ball illuminated by the light source is projected.

The use of several measuring positions on the path of the film has the advantage of permitting greater flexibility of operation.

The electromagnets $E_1$, $E'_1$-$E_2$, $E'_2$-$E_3$, $E'_3$ are excited by a power circuit PR controlled by the processor P so as to generate a magnetic pulse field able to drive the ball BE along an alternative movement at the bottom of the bowl C.

The camera 27 is coupled to the processor C which analyses in real time the image by means of an appropriate software so as to measure the amplitude of the oscillations of the ball BE and determine the critical instant when this amplitude lowers below a specific threshold (for example 50% of the initial amplitude).

Of course, the processor P counts the time between the moment when the reactive agent has been injected into the bowl C and the critical instant so as to deduce from this a coagulation time.

The movements of the film are synchronised with the operating times of each of the stations of the device and in particular with the magnetic field pulses generated by the coils.

The pipette station could possibly be situated at the same location as the measuring station.

Of course, the invention is not limited to the previously described embodiment.

Thus, for example, each infra red/camera source unit could have a field comprising several bowls each excited by a pair of separate electromagnets so as to follow the bowl over a forward distance of several steps with a processor programmed so as to simultaneously detect the movements of the balls of different bowls.

The invention claimed is:

1. A device for driving a series of bowls comprising:
    a series of bowls, each of said bowls comprising a flat-shaped body having a bottom and, opposite said bottom an opening located between two opposing edges extended outwardly at right angles with respect to said body by two respective shoulders provided with two respective protuberances, said shoulders having a shape of an isosceles trapezium having a major base which is integral with the bowl and two oblique edges;
    a film shaped in the form of a tape having two lateral borders parallel to a longitudinal axis these borders being provided with successive pairs of holes respectively formed on the borders, and with trapezoid cuts and teeth having oblique edges forming serrated profiles, each of said protuberances being engaged forcefully in the holes of one said pairs for removably fixing said bowl on said tape with said oblique edges of said shoulders extending in prolongation of oblique edges of said teeth, the teeth of the serrated profiles being hence extended by said shoulders; and
    a notched belt provided with notches which gear between the teeth of the serrated profile extending by said shoulders to ensure a driving with a centering and an indexing of the bowls.

2. The device according to claim 1 wherein said belt is an endless belt guided at each extremity by rollers.

3. The device according to claim 2 wherein at least one of the rollers is driven in rotation by a motor.

4. The device according to claim 1 wherein the notches of said belt are spaced by a distance equal to a multiple of the width of the bowls.

5. The device according to claim 1 which comprises a rail in which said bowls are guided.

6. The device according to claim 5 wherein said rail has a U-shaped cross section
    comprising two vertical wings which are extended at a right angle by two shoulders.

7. The device according to claim 6 wherein the shoulders of said bowl rest on the shoulders of the rail.

* * * * *